United States Patent [19]

Fisher-Cornelssen

[11] 4,085,218
[45] Apr. 18, 1978

[54] ELEVATING MOOD IN GERIATRIC PATIENTS

[75] Inventor: Kurt Anton Fisher-Cornelssen, Oberwil, Switzerland

[73] Assignee: Sandoz Ltd., Basel, Switzerland

[21] Appl. No.: 734,696

[22] Filed: Oct. 21, 1976

[30] Foreign Application Priority Data

Oct. 30, 1975  United Kingdom ............... 44878/75

[51] Int. Cl.² .......................................... A61K 31/445
[52] U.S. Cl. .................................................. 424/267
[58] Field of Search ........................................ 424/267

[56] References Cited

U.S. PATENT DOCUMENTS 3,272,826  9/1966  Jucker et al. .................... 260/293.57

OTHER PUBLICATIONS

Curr. Therap. Res. 10, No. 7, 342–344 (1968).
Dis. Nerv. Syst. 35, No. 1, 35–38 (1974).
Psychopharmacol. Service Center Bull. 5, No. 1 54–55 (1969).
Nervenartz 45, No. 4, 213–214 (1974).

Hollister, Clinical Pharmacology & Therapeutics, vol. 6, No. 5, pp. 555–559, Sept. 1965.
"Depressions and Its Treatment," John Pallitt, Charles C. Thomas, Springfield, Ill. (1965), p. 95.

Primary Examiner—Stanley J. Friedman
Attorney, Agent, or Firm—Gerald D. Sharkin; Robert S. Honor; Thomas O. McGovern

[57] ABSTRACT

The present invention relates to the use of the known compounds of formula

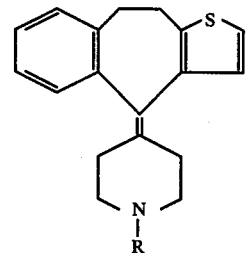

wherein R is lower alkyl, as mood elevating agents for geriatric patients.

11 Claims, No Drawings

ELEVATING MOOD IN GERIATRIC PATIENTS

The present invention relates to known 4-(9,10-dihydro-4H-benzo[4,5]cyclohepta[1,2-b]thiophen-4-yliden)-1-alkyl-piperidine derivatives described and claimed in U.S. Pat. No. 3,272,826, the contents of which are incorporated herein by reference.

More particularly, this invention provides a new use for compounds of formula I,

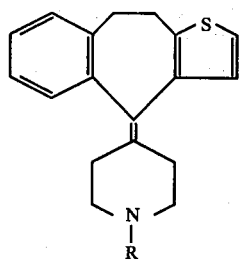

wherein R is lower alkyl.

R preferably signifies alkyl of 1 to 4 carbon atoms, for example, methyl, ethyl, n-propyl and n-butyl, especially methyl.

The compounds of formula I can be prepared according to the process described in the aforementioned U.S. Pat. No.

It has been found that the compounds are useful as mood elevating agents as indicated in standard tests in animals (for example the tetrabenazine antagonism test in rats), where the compounds show a pharmacological profile resembling that of known anti-depressant drugs, and in clinical tests.

The compounds also exhibit specific activity in nonpsychotic depressions and depressive disturbances in geriatric patients. In addition, the compounds are well-tolerated, non-addictive and suited for drug combination, the latter requirement being frequently necessary in geriatric patients.

The compounds are therefore useful as mood elevating agents in geriatric patients, for example, those having a biological age of at least 60. These patients may be either ambulant or non-ambulant, for example, hospitalized.

For the aforementioned use, the dosage to be administered will vary depending on the compound employed, mode of administration and therapy desired. Satisfactory results are obtained at a daily dosage of from about 0.01 mg to about 10 mg/kg, particularly 0.01 to 5 mg/kg animal body weight, conveniently given in divided doses 1 to 8 times a day or in sustained release form. For the larger mammal, the total daily dosage is in the range from about 0.5 to about 25 mg, preferably from about 0.5 to about 12 mg, more preferably from about 3 to about 8 mg, and dosage forms suitable for oral administration comprise from about 0.1 to about 25 mg, preferably from about 0.1 to about 12 mg, more preferably from about 0.4 to about 8 mg of the compounds admixed with a solid or liquid pharmaceutically acceptable diluent or carrier.

The compounds may be administered in free base or in pharmaceutically acceptable acid addition salt form. Such salts possess the same order of activity as the free base forms and are readily prepared in conventional manner. Such salt forms are known and include the hydrogen malate.

The invention also provides a pharmaceutical composition for elevating the mood of geriatric patients, comprising an effective amount of a compound of formula I or a pharmaceutically acceptable acid addition salt form thereof, in association with a pharmaceutically acceptable diluent or carrier.

The compounds may be administered orally in the form of tablets, powders, granules, capsules, dragees, suspensions, syrups or elixirs, or parenterally in the form of injectable solutions or suspensions. Oral administration is preferred. Apart from the active agent, the preparation may contain pharmaceutically inert organic or inorganic adjuvants, optionally filling agents, granulating agents, binding agents, lubricants, dispersing agents, melting agents and preservatives. Moreover, the pharmaceutical preparations may contain colouring, flavouring and sweetening substances, etc. Suitable adjuvants for tablets and capsules are, for example, lactose, microcrystalline cellulose, mannitol, calcium phosphate, starch, alginates, polyvinylpyrrolidone, gelatine, highly dispersed silicic acid, magnesium stearate and talc. Tablet formations may be coated but are preferably uncoated. Suitable suspending agents for the production of liquid administration forms are especially cellulose derivatives, tragacanth and alginates. Suitable wetting agents are, for example, polyoxyethylene stearate and polyoxyethylene sorbitan mono-oleate. Furthermore, preservatives such as p-hydroxy-benzoic acid alkyl ester may be used.

Solid preparations are preferred, especially capsules or dragees, for reasons of easier production and convenience of administration.

The compositions of the invention for internal use suitably contain per unit dosage from about 0.1 mg to about 25 mg, preferably from about 0.1 to about 12 mg, more preferably from about 0.4 to about 8 mg of the compounds. Where the compositions are already in form ready for administration, the concentration of active ingredient in relation to the composition as a whole may naturally vary within large limits, for example from 0.5 to 90%, in particular 3 to 50% by weight. Where the compositions require further working up before administration, as for example with liquid concentrates requiring dilution, the concentrations of the active ingredient are suitably such that, after working up in the required manner, for example dilution, the compositions then contain the active ingredient in the concentrations mentioned above.

The preferred compound of the invention is 4-(9,10-dihydro-4H-benzo[4,5]cyclohepta[1,2-b]thiophen-4-yliden)-1-methyl-piperidine.

In one example, the aforementioned preferred compound in hydrogen malate form is administered in tablets containing 0.5, 1 or 2 mg of said compound at a daily dosage of from 0.5 to 12 mg to a subject in need of mood elevation.

What is claimed is:

1. A method of elevating mood in geriatric patients, which comprises administering to a geriatric patient in need of said treatment a mood elevating effective quantity of a compound of the formula:

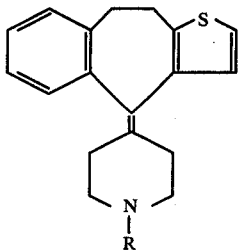

wherein R is lower alkyl,
or a pharmaceutically acceptable acid addition salt form thereof.

2. The method according to claim 1, wherein R is methyl.

3. The method according to claim 1, wherein the compound is in hydrogen malate form.

4. A method according to claim 1 in which the compound is administered at a daily dosage of from 0.01 to 10 milligrams per kilogram of animal body weight.

5. A method according to claim 1 in which the compound is administered at a daily dosage of from 0.01 to 5 milligrams per kilogram of animal body weight.

6. A method according to claim 1 in which 0.5 to 25 milligrams of the compound are administered daily.

7. A method according to claim 1 in which 0.5 to 12 milligrams of the compound are administered daily.

8. A method according to claim 1 in which 3 to 8 milligrams of the compound are administered daily.

9. A method according to claim 1 in which 0.1 to 25 milligrams of the compound are administered per unit dose.

10. A method according to claim 1 in which 0.1 to 12 milligrams of the compound are administered per unit dose.

11. A method according to claim 1 in which 0.4 to 8 milligrams of the compound are administered per unit dose.

* * * * *